(12) United States Patent
Purtzer

(10) Patent No.: US 11,806,488 B2
(45) Date of Patent: Nov. 7, 2023

(54) MEDICAL DEVICE INCLUDING A SOLDERABLE LINEAR ELASTIC NICKEL-TITANIUM DISTAL END SECTION AND METHODS OF PREPARATION THEREFOR

(71) Applicant: Abbott Cardiovascular Systems, Inc., Santa Clara, CA (US)

(72) Inventor: Raleigh A. Purtzer, Temecula, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 313 days.

(21) Appl. No.: 15/670,761

(22) Filed: Aug. 7, 2017

(65) Prior Publication Data

US 2017/0333683 A1 Nov. 23, 2017

Related U.S. Application Data

(63) Continuation of application No. 13/172,278, filed on Jun. 29, 2011, now Pat. No. 9,724,494.

(51) Int. Cl.
*A61M 25/09* (2006.01)
*B23K 35/30* (2006.01)
(Continued)

(52) U.S. Cl.
CPC ............ *A61M 25/09* (2013.01); *B23K 35/007* (2013.01); *B23K 35/025* (2013.01); *B23K 35/30* (2013.01);
(Continued)

(58) Field of Classification Search
CPC ... A61M 25/09; B23K 35/007; B23K 35/025; B23K 35/30; B23K 35/3006;
(Continued)

(56) References Cited

U.S. PATENT DOCUMENTS 2,938,850 A 5/1960 Hans
3,203,884 A 8/1965 Heinz et al.
(Continued)

FOREIGN PATENT DOCUMENTS

CN 101115869 A 1/2008
CN 101554685 A 10/2009
(Continued)

OTHER PUBLICATIONS

Duerig, T. W., Melton, K. N., & Stöckel, D. (2013). *Engineering aspects of shape memory alloys.* Butterworth-Heinemann, 414-419.
(Continued)

*Primary Examiner* — Daniel L Cerioni
(74) *Attorney, Agent, or Firm* — Workman Nydegger; Randy Shen

(57) ABSTRACT

Shapeable guide wire devices and methods for their manufacture. Guide wire devices include an elongate shaft member having a shapeable distal end section that is formed from a linear pseudoelastic nickel-titanium (Ni—Ti) alloy that has linear pseudoelastic behavior without a phase transformation or onset of stress-induced martensite. Linear pseudoelastic Ni—Ti alloy, which is distinct from non-linear pseudoelastic (i.e., superelastic) Ni—Ti alloy, is highly durable, corrosion resistant, and has high stiffness. The shapeable distal end section is shapeable by a user to facilitate guiding the guide wire through tortuous anatomy. In addition, linear pseudoelastic Ni—Ti alloy is more durable tip material than other shapeable tip materials such as stainless steel.

14 Claims, 6 Drawing Sheets

(51) Int. Cl.

| | |
|---|---|
| *B23K 35/00* | (2006.01) |
| *B23K 35/02* | (2006.01) |
| *C22F 1/00* | (2006.01) |
| *C22F 1/10* | (2006.01) |
| *C22F 1/18* | (2006.01) |
| *B23K 103/04* | (2006.01) |
| *B23K 103/14* | (2006.01) |
| *B23K 103/18* | (2006.01) |
| *C21D 7/02* | (2006.01) |

(52) U.S. Cl.
CPC ...... *B23K 35/3006* (2013.01); *B23K 35/3013* (2013.01); *C22F 1/006* (2013.01); *C22F 1/10* (2013.01); *C22F 1/183* (2013.01); *A61M 2025/09083* (2013.01); *A61M 2025/09108* (2013.01); *A61M 2025/09133* (2013.01); *B23K 2103/05* (2018.08); *B23K 2103/14* (2018.08); *B23K 2103/26* (2018.08); *C21D 7/02* (2013.01); *C21D 2201/01* (2013.01); *C21D 2211/001* (2013.01); *C21D 2211/008* (2013.01)

(58) Field of Classification Search
CPC ........ B23K 35/3013; C22F 1/006; C22F 1/10; C22F 1/183
USPC ........................................................ 600/585
See application file for complete search history.

(56) References Cited

U.S. PATENT DOCUMENTS

| | | | |
|---|---|---|---|
| 3,612,058 A | 10/1971 | Ackerman | |
| 3,635,703 A | 1/1972 | Pissarevsky | |
| 3,937,628 A | 2/1976 | Watanabe et al. | |
| 4,127,459 A | 11/1978 | Jumer | |
| 4,330,381 A | 5/1982 | Jumer | |
| 4,654,092 A | 3/1987 | Melton | |
| 4,685,977 A | 8/1987 | Chang | |
| 4,846,186 A | 7/1989 | Box et al. | |
| 4,854,330 A | 8/1989 | Evans, III et al. | |
| 4,967,753 A | 11/1990 | Haase et al. | |
| 5,061,275 A | 10/1991 | Wallsten et al. | |
| 5,067,489 A | 11/1991 | Lind | |
| 5,069,226 A | 12/1991 | Yamauchi et al. | |
| 5,147,317 A | 9/1992 | Shank et al. | |
| 5,171,383 A | 12/1992 | Sagaye et al. | |
| 5,174,295 A | 12/1992 | Christian et al. | |
| 5,174,302 A | 12/1992 | Palmer | |
| 5,184,621 A | 2/1993 | Vogel et al. | |
| 5,238,004 A | 8/1993 | Sahatjian et al. | |
| 5,287,858 A | 2/1994 | Hammerslag et al. | |
| 5,330,826 A | 7/1994 | Taylor et al. | |
| 5,353,798 A | 10/1994 | Sieben | |
| 5,353,808 A | 10/1994 | Viera | |
| 5,354,623 A | 10/1994 | Hall | |
| 5,404,887 A | 4/1995 | Prather | |
| 5,421,955 A | 6/1995 | Lau et al. | |
| 5,433,200 A | 7/1995 | Fleischhacker, Jr. | |
| 5,449,369 A | 9/1995 | Imran | |
| 5,480,382 A | 1/1996 | Hammerslag et al. | |
| 5,514,154 A | 5/1996 | Lau et al. | |
| 5,569,295 A | 10/1996 | Lam | |
| 5,603,721 A | 2/1997 | Lau et al. | |
| 5,618,299 A | 4/1997 | Khosravi et al. | |
| 5,628,787 A | 5/1997 | Mayer | |
| 5,630,840 A | 5/1997 | Mayer | |
| 5,636,641 A | 6/1997 | Fariabi | |
| 5,649,952 A | 7/1997 | Lam | |
| 5,666,969 A | 9/1997 | Urick et al. | |
| 5,673,707 A | 10/1997 | Chandrasekaran | |
| 5,695,111 A | 12/1997 | Nanis et al. | |
| 5,716,400 A | 2/1998 | Davidson | |
| 5,716,417 A | 2/1998 | Girard et al. | |
| 5,725,572 A | 3/1998 | Lam et al. | |
| 5,728,158 A | 3/1998 | Lau et al. | |
| 5,735,893 A | 4/1998 | Lau et al. | |
| 5,746,701 A | 5/1998 | Noone | |
| 5,759,192 A | 6/1998 | Saunders | |
| 5,766,238 A | 6/1998 | Lau et al. | |
| 5,776,080 A | 7/1998 | Thome et al. | |
| 5,788,654 A | 8/1998 | Schwager | |
| 5,797,857 A | 8/1998 | Obitsu | |
| 5,799,386 A | 9/1998 | Ingersoll et al. | |
| 5,803,344 A | 9/1998 | Stankavich et al. | |
| 5,824,077 A | 10/1998 | Mayer | |
| 5,849,037 A | 12/1998 | Frid | |
| 5,858,556 A | 1/1999 | Eckert et al. | |
| 5,865,767 A | 2/1999 | Frechette et al. | |
| 5,876,432 A | 3/1999 | Lau et al. | |
| 5,891,055 A | 4/1999 | Sauter | |
| 5,891,191 A | 4/1999 | Stinson | |
| 5,916,178 A | 6/1999 | Noone et al. | |
| 5,984,973 A | 11/1999 | Girard et al. | |
| 5,985,126 A | 11/1999 | Bleck et al. | |
| 6,004,279 A | 12/1999 | Crowley et al. | |
| 6,027,528 A | 2/2000 | Tomonto et al. | |
| 6,139,511 A | 10/2000 | Huter et al. | |
| 6,183,353 B1 | 2/2001 | Frantzen | |
| 6,214,200 B1 | 4/2001 | Altena et al. | |
| 6,221,096 B1 | 4/2001 | Aiba et al. | |
| 6,234,981 B1 | 5/2001 | Howland | |
| 6,287,331 B1 | 9/2001 | Heath | |
| 6,355,058 B1 | 3/2002 | Pacetti et al. | |
| 6,375,826 B1 | 4/2002 | Wang et al. | |
| 6,390,992 B1 | 5/2002 | Morris et al. | |
| 6,419,693 B1 | 7/2002 | Fariabi | |
| 6,500,130 B2 | 12/2002 | Kinsella et al. | |
| 6,503,290 B1 | 1/2003 | Jarosinski et al. | |
| 6,508,803 B1 | 1/2003 | Horikawa et al. | |
| 6,592,570 B2 | 7/2003 | Abrams et al. | |
| 6,599,415 B1 | 7/2003 | Ku et al. | |
| 6,602,228 B2 | 8/2003 | Nanis et al. | |
| 6,602,272 B2 | 8/2003 | Boylan et al. | |
| 6,610,046 B1 | 8/2003 | Usami et al. | |
| 6,620,192 B1 | 9/2003 | Jalisi | |
| 6,679,980 B1 | 1/2004 | Andreacchi | |
| 7,105,018 B1 | 9/2006 | Yip et al. | |
| 7,156,869 B1 | 1/2007 | Pacetti | |
| 7,208,070 B2 | 4/2007 | Swain | |
| 7,244,319 B2 | 7/2007 | Abrams et al. | |
| 7,250,058 B1 | 7/2007 | Pacetti et al. | |
| 7,252,746 B2 | 8/2007 | Schaeffer | |
| 7,294,214 B2 | 11/2007 | Craig | |
| 7,318,837 B2 | 1/2008 | Krivoruchko et al. | |
| 7,357,854 B1 | 4/2008 | Andreacchi | |
| 7,413,574 B2 | 8/2008 | Yip et al. | |
| 7,488,343 B2 | 2/2009 | O'Brien et al. | |
| 7,494,474 B2 | 2/2009 | Richardson et al. | |
| 7,498,062 B2 | 3/2009 | Calcaterra et al. | |
| 7,501,048 B2 | 3/2009 | Oermans et al. | |
| 7,540,997 B2 | 6/2009 | Stinson | |
| 7,601,230 B2 | 10/2009 | Craig | |
| 7,632,303 B1 | 12/2009 | Stalker et al. | |
| 7,740,798 B2 | 6/2010 | Stinson | |
| 7,771,581 B2 | 8/2010 | Callol et al. | |
| 7,785,274 B2 | 8/2010 | Mishima et al. | |
| 7,883,474 B1 | 2/2011 | Mirigian et al. | |
| 8,100,837 B1 | 1/2012 | Cornish et al. | |
| 8,267,872 B2 | 9/2012 | Ressemann et al. | |
| 8,323,459 B2 | 12/2012 | Andreacchi et al. | |
| 8,348,860 B2 | 1/2013 | Murayama et al. | |
| 8,360,995 B2 | 1/2013 | Elsesser et al. | |
| 8,430,923 B2 | 4/2013 | Pacetti et al. | |
| 8,529,710 B2 | 9/2013 | Ishida et al. | |
| 8,591,672 B2 | 11/2013 | Janko et al. | |
| 8,790,393 B2 | 7/2014 | Bregulla et al. | |
| 8,808,618 B2 | 8/2014 | Furst et al. | |
| 8,815,061 B2 | 8/2014 | Andreacchi et al. | |
| 8,852,264 B2 | 10/2014 | Pacetti et al. | |
| 9,045,843 B2 | 6/2015 | Andreacchi et al. | |
| 9,133,563 B2 | 9/2015 | Andreacchi | |
| 9,145,619 B2 | 9/2015 | Andreacchi et al. | |
| 9,566,147 B2 | 2/2017 | Kramer-Brown et al. | |

(56) References Cited

U.S. PATENT DOCUMENTS

| | | |
|---|---|---|
| 9,566,174 B1 | 2/2017 | De et al. |
| 9,592,135 B2 | 3/2017 | Thompson |
| 9,668,890 B2 | 6/2017 | Ma et al. |
| 10,441,445 B2 | 10/2019 | Kramer-Brown et al. |
| 10,617,541 B2 | 4/2020 | Nishigishi |
| 10,835,393 B2 | 11/2020 | Ma et al. |
| 11,141,296 B2 | 10/2021 | Thompson |
| 11,298,251 B2 | 4/2022 | Simpson et al. |
| 2001/0009981 A1 | 7/2001 | DuBois et al. |
| 2002/0032477 A1 | 3/2002 | Helmus et al. |
| 2002/0062092 A1 | 5/2002 | Muni et al. |
| 2002/0082524 A1 | 6/2002 | Anderson et al. |
| 2002/0087099 A1* | 7/2002 | Nanis ............... A61L 31/022 600/585 |
| 2003/0102360 A1 | 6/2003 | Eungard et al. |
| 2003/0120181 A1 | 6/2003 | Toma et al. |
| 2003/0125642 A1 | 7/2003 | Kato et al. |
| 2003/0134142 A1 | 7/2003 | Ivey et al. |
| 2004/0111044 A1 | 6/2004 | Davis et al. |
| 2004/0129347 A1 | 7/2004 | Craig |
| 2004/0167436 A1 | 8/2004 | Reynolds et al. |
| 2004/0167442 A1 | 8/2004 | Shireman et al. |
| 2004/0181175 A1 | 9/2004 | Clayman et al. |
| 2004/0225231 A1 | 11/2004 | Ehr |
| 2004/0236433 A1 | 11/2004 | Kennedy et al. |
| 2004/0243168 A1 | 12/2004 | Ferrera et al. |
| 2004/0267351 A1 | 12/2004 | Swain |
| 2005/0054952 A1 | 3/2005 | Eskuri et al. |
| 2005/0056687 A1* | 3/2005 | Matsumoto ......... H05K 3/3485 228/248.1 |
| 2005/0059889 A1 | 3/2005 | Mayer |
| 2005/0060025 A1 | 3/2005 | Mackiewicz et al. |
| 2005/0070997 A1 | 3/2005 | Thornton et al. |
| 2005/0096568 A1 | 5/2005 | Kato |
| 2005/0098444 A1 | 5/2005 | Schaeffer |
| 2005/0124917 A1 | 6/2005 | Skujins et al. |
| 2005/0137501 A1 | 6/2005 | Euteneuer et al. |
| 2005/0145307 A1 | 7/2005 | Shireman et al. |
| 2005/0145508 A1 | 7/2005 | Arsen et al. |
| 2005/0263171 A1 | 12/2005 | Wu et al. |
| 2005/0263717 A1 | 12/2005 | Soluri et al. |
| 2005/0267385 A1 | 12/2005 | Hofmann et al. |
| 2005/0273021 A1 | 12/2005 | Burgermeister |
| 2005/0273156 A1 | 12/2005 | Burgermeister et al. |
| 2005/0288773 A1 | 12/2005 | Glocker et al. |
| 2006/0079954 A1 | 4/2006 | Burgermeister et al. |
| 2006/0122537 A1 | 6/2006 | Reynolds et al. |
| 2006/0190070 A1 | 8/2006 | Dieck et al. |
| 2006/0241519 A1 | 10/2006 | Hojeibane et al. |
| 2006/0259126 A1 | 11/2006 | Jason |
| 2006/0264784 A1 | 11/2006 | Lupton |
| 2006/0271169 A1 | 11/2006 | Ye et al. |
| 2006/0272751 A1 | 12/2006 | Kato |
| 2006/0287709 A1 | 12/2006 | Rao |
| 2007/0034527 A1 | 2/2007 | Diaz et al. |
| 2007/0034528 A1 | 2/2007 | Diaz et al. |
| 2007/0135891 A1 | 6/2007 | Schneider |
| 2007/0156215 A1 | 7/2007 | Jensen et al. |
| 2007/0173925 A1 | 7/2007 | Fliedner |
| 2007/0185415 A1 | 8/2007 | Ressemann et al. |
| 2007/0185564 A1 | 8/2007 | Pacetti et al. |
| 2007/0198044 A1 | 8/2007 | Lupton et al. |
| 2007/0209947 A1 | 9/2007 | Shrivastava et al. |
| 2007/0219464 A1 | 9/2007 | Davis et al. |
| 2007/0219465 A1 | 9/2007 | Cedro et al. |
| 2007/0219624 A1 | 9/2007 | Brown et al. |
| 2007/0244413 A1 | 10/2007 | Biggins |
| 2007/0249964 A1 | 10/2007 | Richardson et al. |
| 2007/0249965 A1 | 10/2007 | Abrams et al. |
| 2007/0265699 A1 | 11/2007 | Grewe et al. |
| 2007/0270942 A1 | 11/2007 | Thomas |
| 2008/0004546 A1 | 1/2008 | Kato |
| 2008/0033522 A1 | 2/2008 | Grewe et al. |
| 2008/0070058 A1 | 3/2008 | Dasgupta et al. |
| 2008/0077049 A1 | 3/2008 | Hirshman |
| 2008/0091267 A1 | 4/2008 | Stinson et al. |
| 2008/0097248 A1 | 4/2008 | Munoz et al. |
| 2008/0146967 A1 | 6/2008 | Richardson et al. |
| 2008/0160259 A1 | 7/2008 | Nielson et al. |
| 2008/0161726 A1 | 7/2008 | Itou |
| 2008/0177371 A1 | 7/2008 | Ryan et al. |
| 2008/0183280 A1 | 7/2008 | Agnew et al. |
| 2008/0200879 A1 | 8/2008 | Isi et al. |
| 2008/0208308 A1 | 8/2008 | Allen et al. |
| 2008/0208352 A1 | 8/2008 | Krivoruchko et al. |
| 2008/0215132 A1 | 9/2008 | Ryan et al. |
| 2008/0228109 A1 | 9/2008 | Kinoshita et al. |
| 2008/0234605 A1 | 9/2008 | Urie |
| 2008/0257717 A1 | 10/2008 | Vacheron |
| 2008/0262600 A1 | 10/2008 | Jalisi |
| 2008/0281230 A1 | 11/2008 | Kinoshita et al. |
| 2008/0312747 A1 | 12/2008 | Cameron et al. |
| 2009/0000105 A1 | 1/2009 | Kato |
| 2009/0030500 A1 | 1/2009 | Weber et al. |
| 2009/0048659 A1 | 2/2009 | Weber et al. |
| 2009/0093871 A1 | 4/2009 | Rea et al. |
| 2009/0112127 A1 | 4/2009 | Keating et al. |
| 2009/0118675 A1 | 5/2009 | Czyscon et al. |
| 2009/0118822 A1 | 5/2009 | Holman et al. |
| 2009/0149947 A1 | 6/2009 | Frohwitter |
| 2009/0163833 A1 | 6/2009 | Kinoshita et al. |
| 2009/0204203 A1 | 8/2009 | Allen et al. |
| 2009/0227902 A1 | 9/2009 | Simpson et al. |
| 2009/0240324 A1 | 9/2009 | Smith |
| 2009/0254000 A1 | 10/2009 | Layman et al. |
| 2009/0255827 A1 | 10/2009 | Andreacchi et al. |
| 2009/0258050 A1 | 10/2009 | Lindsay et al. |
| 2009/0259299 A1 | 10/2009 | Moloney |
| 2009/0276033 A1 | 11/2009 | Mayer |
| 2010/0004562 A1 | 1/2010 | Jalisi et al. |
| 2010/0004733 A1 | 1/2010 | Atanasoska et al. |
| 2010/0049304 A1 | 2/2010 | Clifford et al. |
| 2010/0158426 A1 | 6/2010 | Manipatruni et al. |
| 2010/0158436 A1 | 6/2010 | Riska |
| 2010/0217373 A1 | 8/2010 | Boyle et al. |
| 2010/0222866 A1 | 9/2010 | Wachter et al. |
| 2010/0222873 A1 | 9/2010 | Atanasoska et al. |
| 2010/0241210 A1 | 9/2010 | Patadia |
| 2010/0249654 A1* | 9/2010 | Elsesser ............... A61M 25/09 600/585 |
| 2010/0262227 A1 | 10/2010 | Rangwala et al. |
| 2011/0062031 A1 | 3/2011 | Wulf |
| 2011/0066106 A1 | 3/2011 | Kato |
| 2011/0106236 A1 | 5/2011 | Su et al. |
| 2011/0118628 A1 | 5/2011 | Zhou et al. |
| 2011/0247943 A1 | 10/2011 | Bialas et al. |
| 2011/0264161 A1 | 10/2011 | Schiefer et al. |
| 2011/0319872 A1 | 12/2011 | Kawasaki |
| 2011/0319980 A1 | 12/2011 | Ryan |
| 2012/0016458 A1 | 1/2012 | Abunassar |
| 2012/0041342 A1 | 2/2012 | Purtzer |
| 2012/0065623 A1 | 3/2012 | Nelson, III et al. |
| 2012/0109108 A1 | 5/2012 | Boyle et al. |
| 2012/0123525 A1 | 5/2012 | Kramer-Brown et al. |
| 2012/0199489 A1 | 8/2012 | Vacheron |
| 2012/0282571 A1* | 11/2012 | Ammon ............... C21D 6/007 433/102 |
| 2013/0006149 A1 | 1/2013 | Purtzer |
| 2013/0006222 A1 | 1/2013 | Nabeshima et al. |
| 2013/0013055 A1 | 1/2013 | Pacetti et al. |
| 2013/0092554 A1 | 4/2013 | Wong et al. |
| 2013/0092556 A1 | 4/2013 | Wong et al. |
| 2013/0092557 A1 | 4/2013 | Wong et al. |
| 2013/0204353 A1 | 8/2013 | Kramer-Brown et al. |
| 2013/0241112 A1 | 9/2013 | Jow |
| 2014/0014530 A1 | 1/2014 | Zhicheng |
| 2014/0076719 A1 | 3/2014 | Andreacchi et al. |
| 2014/0076720 A1 | 3/2014 | Andreacchi et al. |
| 2014/0076737 A1 | 3/2014 | Andreacchi et al. |
| 2014/0076739 A1 | 3/2014 | Andreacchi |
| 2014/0155979 A1 | 6/2014 | Am et al. |
| 2014/0271319 A1 | 9/2014 | Zheng et al. |

(56) References Cited

U.S. PATENT DOCUMENTS

| | | |
|---|---|---|
| 2014/0360887 A1 | 12/2014 | Andreacchi et al. |
| 2016/0002816 A1 | 1/2016 | Andreacchi |
| 2017/0296365 A1 | 10/2017 | Kramer-Brown et al. |

FOREIGN PATENT DOCUMENTS

| | | | |
|---|---|---|---|
| CN | 102356185 A | | 2/2012 |
| CN | 102481662 A | | 5/2012 |
| CN | 102552991 A | | 7/2012 |
| CN | 202412010 U | | 9/2012 |
| CN | 103252496 A | | 8/2013 |
| CN | 110306099 A | | 10/2019 |
| EP | 0804934 A2 | | 11/1997 |
| EP | 1604691 A2 | | 12/2005 |
| EP | 1632584 A1 | | 3/2006 |
| EP | 1674118 A2 | | 6/2006 |
| EP | 1 731 241 | | 12/2006 |
| EP | 1829982 A1 | | 9/2007 |
| EP | 2054101 A2 | | 5/2009 |
| EP | 2640432 | | 5/2012 |
| EP | 2676684 A1 | | 12/2013 |
| EP | 2676686 A1 | | 12/2013 |
| EP | 3138587 A1 | | 8/2017 |
| JP | 07-090694 A | | 4/1995 |
| JP | 08-302500 A | | 11/1996 |
| JP | H09508538 | | 9/1997 |
| JP | 2002503529 | | 2/2002 |
| JP | 2002069555 | | 3/2002 |
| JP | 2003267609 | | 9/2003 |
| JP | 2006519068 | | 8/2006 |
| JP | 2008188670 | | 8/2008 |
| WO | 97/33534 A1 | | 9/1997 |
| WO | 99/15108 A2 | | 4/1999 |
| WO | 00/54704 A1 | | 9/2000 |
| WO | 00/69368 A2 | | 11/2000 |
| WO | 01/15632 A1 | | 3/2001 |
| WO | 01/17577 A1 | | 3/2001 |
| WO | 01/61080 A1 | | 8/2001 |
| WO | 01/72349 A1 | | 10/2001 |
| WO | 02/78763 | | 10/2002 |
| WO | 2007/103446 A2 | | 9/2007 |
| WO | WO 2008/022126 | | 2/2008 |
| WO | 2009/126431 A2 | | 10/2009 |
| WO | 2010/081723 A1 | | 7/2010 |
| WO | WO 2010/107798 | | 9/2010 |
| WO | 2012/068358 A1 | | 5/2012 |
| WO | 2013/162690 A1 | | 10/2013 |
| WO | 2014/159743 A1 | | 10/2014 |
| WO | 2014/159747 A1 | | 10/2014 |

OTHER PUBLICATIONS

Eutectic system. In *Wikipedia, The Free Encyclopedia*. Retrieved 11:54, Apr. 27, 2010, 1-5, from https://en.wikipedia.org/w/index.php?title=Eutectic_system&oldid=702728275.

Gold. In *Wikipedia, The Free Encyclopedia*. Revised on Apr. 22, 2010, Retrieved 11:11, Aug. 7, 2017, 1-21, from https://en.wikipedia.org/w/index.php?title=Gold&diff=357659233&oldid=357425502.

Indium. In *Wikipedia, The Free Encyclopedia*. Retrieved 12:13, Apr. 27, 2010, 1-7, from https://en.wikipedia.org/w/index.php?title=Indium&oldid=706790732.

Jacobson, D. M., & Humpston, G. (1989). Gold coatings for fluxless soldering. *Gold Bulletin*, 22(1), 9-18.

Tin. In *Wikipedia, The Free Encyclopedia*. Retrieved 12:08, Apr. 27, 2010, 1-15, from https://en.wikipedia.org/w/index.php?title=Tin&oldid=708568728.

U.S. Appl. No. 13/172,278, filed Jun. 10, 2013 Office Action.
U.S. Appl. No. 13/172,278, filed Nov. 21, 2013 Office Action.
U.S. Appl. No. 13/172,278, filed Apr. 3, 2015 Office Action.
U.S. Appl. No. 13/172,278, filed Oct. 8, 2015 Office Action.
U.S. Appl. No. 13/172,278, filed Sep. 19, 2016 Office Action.
U.S. Appl. No. 13/172,278, filed Apr. 11, 2017 Notice of Allowance.
U.S. Appl. No. 13/172,278, filed Jul. 19, 2017 Issue Notification.

Narushima, Precipitates-in-Biomedical-Co-Cr-Alloys_Narushima-Mineta-Kurihara-Ueda_Publishedonline-February26,2013, Feb. 26, 2013, JOM, Vol. 65, No. 4, 2013, 489, 65.

Campbell, ed. Chapter 16 Nonequilbrium Reactions-Precipitation Hardening. Phase Diagrams Understanding the Basics. ASM International. 2012. 339-361. (Year: 2012).

CN 101554685 machine translation (Year: 2009).
CN 103252496 machine translation (Year: 2013).
CN 110306099 machine translation (Year: 2019).

Cordis Palmaz Blue 018 Peripheral Stent System, Johson & Johnson Medical NV/SA, May 2005 (2 pages) http://www.jjnordic.com/Lists/FileList1/Attatchments/174/PalmazBlue.sub .- - 018.sub .-Brochure.PDF.

Dinega, Dmitry P., and M. G. Bawendi. "A solution-phase chemical approach to a new crystal structure of cobalt." Angewandte Chemie International Edition 38.12 (1999): 1788-1791.

Donachie et al. Chapter 7 Powder Metallurgy Processing. Superalloys A Technical Guide. Second Edition. 2002. ASM International. 117-134. (Year: 2002).

Final Office Action received for U.S. Appl. No. 16/601,259, dated Sep. 23, 2021, 11 pages.

Forging of Niobium, tantalum, and their alloys, MetalPass, accessed Apr. 18, 2013. http://www.metalpass.com/metaldoc/paper.aspx?docID=312.

Giessen et al., "Coronary Stenting with a New Radiopaque Balloon Expandable Endoprosthesis in Pigs", Circulation, vol. 83, No. 5, May 1991, pp. 1788-1798.

International Search Report and Written Opinion of the International Searching Authority dated Sep. 26, 2007, for related PCT Application No. PCT/US2007/05844.

Issue Notification received for U.S. Appl. No. 09/534,071, mailed on Jul. 11, 2007.

Issue Notification received for U.S. Appl. No. 13/548,908 mailed on Mar. 11, 2015.

Issue Notification received for U.S. Appl. No. 13/618,602, mailed on Sep. 17, 2014.

Liu. 2 Processes and Techniques for Droplet Generation. Science and Engineering of Droplets. Notes Publications. 2000. 19-120. (Year: 2000).

Non-Final Office Action received for U.S. Appl. No. 16/601,259, dated May 17, 2021, 11 pages.

Non-Final Office Action received for U.S. Appl. No. 17/068,526, mailed on Oct. 5, 2022, 35 pages.

Notice of Allowance received for U.S. Appl. No. 09/534,071, mailed on Feb. 12, 2007.

Notice of Allowance received for U.S. Appl. No. 11/736,979, mailed on Nov. 9, 2012.

Notice of Allowance received for U.S. Appl. No. 12/100,991 mailed on Aug. 17, 2012.

Notice of Allowance received for U.S. Appl. No. 13/548,908 mailed on Dec. 2, 2014.

Notice of Allowance received for U.S. Appl. No. 13/617,877, mailed on May 28, 2015.

Notice of Allowance received for U.S. Appl. No. 13/618,348 mailed on Aug. 6, 2014.

Notice of Allowance received for U.S. Appl. No. 13/618,455, mailed on Feb. 2, 2015.

Notice of Allowance received for U.S. Appl. No. 14/466,513, mailed on Mar. 28, 2017.

Notice of Allowance received for U.S. Appl. No. 16/601,259, mailed on Dec. 6, 2021, 8 pages.

Notice of Allowance received for U.S. Appl. No. 16/601,259, mailed on Mar. 9, 2022, 6 pages.

Notice of Allowance received for U.S. Appl. No. 11/370,642 mailed on Apr. 12, 2010.

Notice of Allowance received for U.S. Appl. No. 13/618,602, mailed on May 27, 2014.

Notice of Allowance received for U.S. Appl. No. 13/830,404, mailed on Oct. 18, 2016.

Notice of Allowance received for U.S. Appl. No. 15/429,339, mailed on Jun. 5, 2019.

(56) References Cited

OTHER PUBLICATIONS

Notification of Transmittal of the International Search Report and the Written Opinion of the International Searching Authority, or the Declaration, Patent Cooperation Treaty, European Patent Office, Dec. 29, 2009 (12 pages).
Office Action received for U.S. Appl. No. 09/534,071, dated Aug. 29, 2005.
Office Action received for U.S. Appl. No. 09/534,071, dated Dec. 18, 2002.
Office Action received for U.S. Appl. No. 09/534,071, dated Mar. 13, 2006.
Office Action received for U.S. Appl. No. 09/534,071, dated Nov. 15, 2005.
Office Action received for U.S. Appl. No. 09/534,071, dated Sep. 13, 2006.
Office Action received for U.S. Appl. No. 09/534,071, dated Sep. 17, 2002.
Office Action received for U.S. Appl. No. 11/370,642 dated Sep. 22, 2009.
Office Action received for U.S. Appl. No. 11/736,979, dated Apr. 4, 2011.
Office Action received for U.S. Appl. No. 11/736,979, dated Apr. 12, 2012.
Office Action received for U.S. Appl. No. 11/736,979, dated Aug. 31, 2010.
Office Action received for U.S. Appl. No. 11/736,979, dated May 26, 2010.
Office Action received for U.S. Appl. No. 11/736,979, dated Sep. 19, 2011.
Office Action received for U.S. Appl. No. 12/100,991 dated Dec. 21, 2011.
Office Action received for U.S. Appl. No. 12/100,991 dated Sep. 29, 2011.
Office Action received for U.S. Appl. No. 13/271,869 dated Apr. 26, 2013.
Office Action received for U.S. Appl. No. 13/271,869 dated Nov. 27, 2013.
Office Action received for U.S. Appl. No. 13/548,908 dated Jun. 18, 2014.
Office Action received for U.S. Appl. No. 13/618,407, dated Dec. 2, 2014.
Office Action received for U.S. Appl. No. 13/618,455 dated May 8, 2014.
Office Action received for U.S. Appl. No. 13/618,455 dated Sep. 25, 2014.
Office Action received for U.S. Appl. No. 13/618,602, dated May 3, 2013.
Office Action received for U.S. Appl. No. 09/534,071, dated Jul. 9, 2003.
Office Action received for U.S. Appl. No. 13/298,070, dated Jun. 25, 2014.
Office Action received for U.S. Appl. No. 13/298,070, dated Oct. 6, 2014.
Office Action received for U.S. Appl. No. 13/618,602, dated Aug. 20, 2013.
Office Action received for U.S. Appl. No. 13/618,602, dated Jan. 6, 2014.
Office Action received for U.S. Appl. No. 13/830,404, dated Apr. 20, 2016.
Office Action received for U.S. Appl. No. 13/830,404, dated Aug. 10, 2016.
Office Action received for U.S. Appl. No. 13/830,404, dated Jan. 8, 2016.
Office Action received for U.S. Appl. No. 13/830,404, dated May 29, 2015.
Office Action received for U.S. Appl. No. 13/830,404, dated Sep. 16, 2015.
Office Action received for U.S. Appl. No. 15/429,339, dated Feb. 26, 2019.
Ohring et al. "A Versatile Arc Melting Apparatus for Quenching Molten Metals and Ceramics." Review of Scientific instruments 42.4 (1971): 530-531.
Poletti et al. Development of a new high entropy alloy for wear resistance: FeCoCrNiWO.3 and FeCoCrNiW0.3+5 at% of C. Materials and Design 115 (2017) 247-254. (Year: 2017).
Restriction Requirement received for U.S. Appl. No. 13/618,602, mailed on Mar. 4, 2013.
Restriction Requirement received for U.S. Appl. No. 17/068,526, mailed on Jul. 15, 2022, 6 pages.
Restriction Requirement received for U.S. Appl. No. 13/298,070, mailed on May 2, 2014.
Shang. CoCrFeNi(W1-xMox) high-entropy alloy coatings with excellent mechanical properties and corrosion resistance prepared by mechanical alloying and hot pressing sintering. Materials and Design 117 (2017) 193-202. (Year: 2017).
Sheng. A Co-Cr-Ni-W-C alloy processed by multiple rolling. Strength of Materials, vol. 52, No. 1, Jan. 2020. (Year: 2020).
Tanaka. Effects of high-temperature ageing on the creep-rupture properties of high-tungsten cobalt-base superalloys. Journal of Materials Science 29 (1994) 2620-2628. (Year: 1994).
U.S. Appl. No. 11/370,642, filed Apr. 12, 2010, Notice of Allowance.
U.S. Appl. No. 11/370,642, filed Sep. 22, 2009, Office Action.
U.S. Appl. No. 11/736,979, filed Apr. 10, 2013, Issue Notification.
U.S. Appl. No. 13/271,869, filed Apr. 1, 2013, Office Action.
U.S. Appl. No. 13/271,869, filed Apr. 26, 2013, Office Action.
U.S. Appl. No. 13/271,869, filed Jul. 9, 2014, Issue Notification.
U.S. Appl. No. 13/271,869, filed Mar. 18, 2014, Notice of Allowance.
U.S. Appl. No. 13/271,869, filed Nov. 27, 2013, Office Action.
U.S. Appl. No. 13/617,877, filed Dec. 20, 2013, Office Action.
U.S. Appl. No. 13/617,877, filed Sep. 23, 2014, Office Action.
U.S. Appl. No. 13/618,348, filed Dec. 19, 2013, Office Action.
U.S. Appl. No. 13/618,348, filed Sep. 14, 2012, Anthony S. Andreacchi, Aug. 6, 2014, Issue Notification.
U.S. Appl. No. 13/618,348, Mail Date Apr. 16, 2014, Notice of Allowance.
U.S. Appl. No. 13/618,407, Mail Date May 13, 2015, Notice of Allowance.
U.S. Appl. No. 13/618,455, filed Sep. 14, 2012, Andreacchi et al.
U.S. Appl. No. 13/618,455, Mail Date May 13, 2015, Issue Notification.
U.S. Appl. No. 11/736,979, filed Feb. 20, 2013, Issue Notification.
Wang et al. Microstructure and mechanical properties of CoCrFeNiWx high entropy alloys reinforced by u phase particles. Journal of Alloys and Compounds 843 (2020) 155997. (Year: 2020).
Zhang et al. Phase transformations in Co-Ni-Cr-W alloys during high temperature exposure to steam environment. J. Phase Equil. Diffus. (2018) 39:387-400. (Year: 2018).

\* cited by examiner

MEDICAL DEVICE INCLUDING A SOLDERABLE LINEAR ELASTIC NICKEL-TITANIUM DISTAL END SECTION AND METHODS OF PREPARATION THEREFOR

CROSS-REFERENCE TO RELATED APPLICATIONS

This application is a continuation of U.S. patent application Ser. No. 13/172,278, filed 29 Jun. 2011, the disclosure of which is incorporated herein by reference in its entirety.

BACKGROUND

1. The Field of the Invention

The present invention relates to guide wires, particularly to guide wires used to guide a catheter in a body lumen such as a blood vessel.

2. The Relevant Technology

Guide wires are used to guide a catheter for treatment of intravascular sites, such as percutaneous transluminal coronary angioplasty ("PTCA"), or in examination such as cardio-angiography. A guide wire used in the PTCA is inserted into the vicinity of a target angiostenosis portion together with a balloon catheter, and is operated to guide the distal end portion of the balloon catheter to the target angiostenosis portion.

A guide wire needs appropriate flexibility, pushability and torque transmission performance for transmitting an operational force from the proximal end portion to the distal end, and kink resistance (resistance against sharp bending). To meet such requirements, superelastic materials such as a Ni—Ti alloy and high strength materials have been used for forming a core member (i.e., a wire body) of a guide wire.

Near equiatomic binary nickel-titanium alloys are known to exhibit "pseudoelastic" behavior when given certain cold working processes or cold working and heat treatment processes following hot working. Pseudoelasticity can be further divided into two subcategories: "linear" pseudoelasticity and "non-linear" pseudoelasticity. "Non-linear" pseudoelasticity is sometimes used by those in the industry synonymously with "superelasticity."

Linear pseudoelasticity typically results from cold working. Non-linear pseudoelasticity results from cold working and subsequent heat treatment. Non-linear pseudoelasticity, in its idealized state, exhibits a relatively flat loading plateau in which a large amount of recoverable strain is possible with very little increase in stress. This flat plateau can be seen in the stress-strain hysteresis curve of the alloy. Linear pseudoelasticity exhibits no such flat plateau. Non-linear pseudoelasticity is known to occur due to a reversible phase transformation from austenite to martensite, the latter more precisely called stress-induced martensite ("SIM"). Linear pseudoelastic materials exhibit no such phase transformation. Linear pseudoelastic nickel titanium alloy can be permanently deformed or shaped by overstressing the alloy above a plateau stress that is at least partially dependent on the amount of cold-worked martensite structure present in the linear pseudoelastic structure. This is in marked contrast to non-linear pseudoelastic nickel titanium alloy, which cannot be permanently deformed by overstressing.

BRIEF SUMMARY

The present disclosure describes guide wire devices and methods for their manufacture. Guide wire devices described herein include an elongate shaft member having a shapeable distal end section that is formed from a linear pseudoelastic nickel-titanium (Ni—Ti) alloy that has linear pseudoelastic behavior without a phase transformation or onset of stress-induced martensite. Linear pseudoelastic Ni—Ti alloy, which is distinct from non-linear pseudoelastic (i.e., superelastic) Ni—Ti alloy, is highly durable, corrosion resistant, and has high stiffness. The shapeable distal end section is shapeable by a user to facilitate guiding the guide wire through tortuous anatomy. In addition, linear pseudoelastic Ni—Ti alloy is more durable tip material than other shapeable tip materials such as stainless steel. This may, for example, allow practitioners to use one wire to treat multiple lesions, potentially reducing costs and procedure time.

In one embodiment, a shapeable guide wire device is described. The shapeable guide wire device includes an elongate shaft member that includes a proximal end section and a shapeable distal end section having a solder material applied thereto, wherein the shapeable distal end section includes a cold-worked nickel titanium alloy exhibiting linear pseudoelasticity. The shapeable guide wire device further includes a helical coil section disposed about at least the shapeable distal end section and an atraumatic cap section attached to the helical coil section and the solder material of the shapeable distal end section via a soldered joint. According to the present disclosure, the soldered joint is formed without substantial loss of the linear pseudoelasticity of the shapeable distal end section.

In another embodiment, a method for fabricating a guide wire device is disclosed. The method includes (1) fabricating an elongate shaft member that includes a proximal end section and a distal end section. In one embodiment, the distal end section includes a distal nickel-titanium alloy member that has a first cross-sectional dimension. The method further includes (2) applying a solder material to at least a portion of the distal end section, (3) cold working at least a portion of the distal end section having the solder material applied thereto, wherein the cold working yields a distal shapeable end section having a second cross-sectional dimension and linear pseudoelastic deformation behavior, and (4) soldering the distal shapeable section and a helical coil section disposed about the distal shapeable section to an atraumatic cap without substantial loss of the linear pseudoelasticity of the distal shapeable section.

In one embodiment, fabricating an elongate shaft member that includes a proximal end section and a distal end section may include attaching (e.g., by welding) a proximal end section fabricated from a first material such as stainless steel to a distal end section fabricated from a second material such as nickel-titanium alloy. Alternatively, the elongate shaft member can be fabricated from a single material such as, but not limited to, a nickel-titanium alloy.

In one embodiment, fabricating an elongate shaft member may further include drawing at least a portion of the elongate shaft member through a drawing die, rolling, calendaring, or grinding to form or reshape the at least a portion of the elongate shaft member and cleaning the elongate shaft member such as by ultrasonically cleaning.

Ni—Ti alloys, such as those described herein, are very difficult to solder due to the formation of a tenacious, naturally occurring oxide coating which prevents the molten solder from wetting the surface of the alloy. It has been found that by first treating the surface of the refractory superelastic alloy with molten alkali metal hydroxide, e.g., sodium, potassium, lithium or mixtures thereof to form a nascent alloy surface and then pretinning (i.e., applying a suitable solder material, such as, a gold-tin solder, a gold-indium solder, a gold-germanium solder, a silver-tin solder, a silver-gold-tin solder, or another suitable solder) without contacting air, that Ni—Ti alloys can be readily soldered in a conventional manner. In one embodiment, solder can be applied to at least a portion of the distal end section by dipping the at least the distal end section into a bath of a molten solder material, wherein the bath of molten solder material includes an upper layer of a molten metal hydroxide and a lower layer of the molten solder material.

Subsequently, at least a portion of the distal end section, with the solder material applied thereto, can be cold-worked to yield a distal shapeable end section having a second cross-sectional dimension. After applying the solder material and cold working, a helical coil section can be assembled around the a distal portion of the elongate shaft member, including the distal shapeable section, and a rounded plug (i.e., an aturaumatic cap section) can be formed at the distal end of the assembly by soldering the distal shapeable section and a helical coil section disposed about the distal shapeable section to the rounded plug without substantial loss of the linear pseudoelasticity of the distal shapeable section. The pretinning followed by cold working and forming the atraumatic cap at the distal end of the elongate shaft member yields a user-shapeable distal end section that exhibits linear pseudoelastic deformation behavior without a phase transformation or onset of stress-induced martensite.

In a more specific embodiment, a method for fabricating a guide wire device that has a shapeable distal end section is disclosed. The method includes (1) providing an elongate shaft member that includes a proximal end section and a distal end section, wherein the distal end section includes a nickel-titanium alloy member, (2) grinding at least a portion of the distal end section to a first cross-sectional dimension, and (3) ultrasonically cleaning at least the distal end section. After grinding and cleaning, the method further includes (4) dipping at least a portion of the distal end section into a bath of a molten solder material, wherein the bath of molten solder material includes an upper layer of a molten metal hydroxide and a lower layer of the molten solder material, and (5) cold working at least a portion of the distal end section, wherein the cold working yields a distal shapeable section having a linear pseudoelastic nickel-titanium microstructure. After cold working at least a portion of the distal end section, the method continues with (6) ultrasonically cleaning at least the distal end section, (7) disposing a helical coil section about the distal shapeable section, and (8) forming an atraumatic cap section coupling the helical coil section and the distal shapeable section via a soldered joint, wherein the soldered joint is formed without loss of the linear elastic nickel-titanium microstructure.

These and other objects and features of the present disclosure will become more fully apparent from the following description and appended claims, or may be learned by the practice of embodiments of the invention as set forth hereinafter.

BRIEF DESCRIPTION OF THE DRAWINGS

To further clarify the above and other advantages and features of the present disclosure, a more particular description of the embodiments of the invention will be rendered by reference to the appended drawings. It is appreciated that these drawings depict only illustrated embodiments of the invention and are therefore not to be considered limiting of its scope. The embodiments of the invention will be described and explained with additional specificity and detail through the use of the accompanying drawings in which.

DETAILED DESCRIPTION

I. Introduction

Figure 1A:
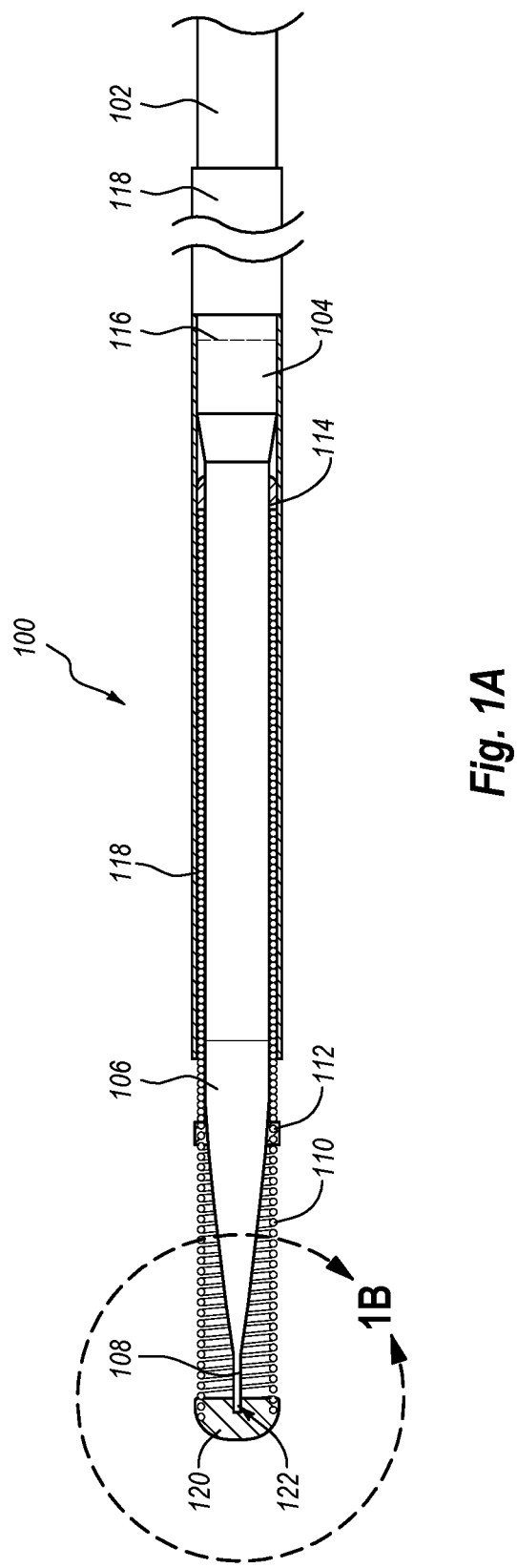
FIG. 1A illustrates a partial cut-away view of a guide wire device according to one embodiment of the present invention.

The present disclosure describes guide wire devices and methods for their manufacture. Guide wire devices disclosed herein include an elongate shaft member having a shapeable distal end section that is formed from a linear pseudoelastic nickel-titanium (Ni—Ti) alloy that has linear pseudoelastic behavior without the onset of stress-induced martensite during deformation. Linear pseudoelastic Ni—Ti alloy, which is distinct from non-linear pseudoelastic (i.e., superelastic) Ni—Ti alloy, is highly durable, corrosion resistant, and has a relatively high stiffness. Linear pseudoelastic Ni—Ti is in the martensite phase at body temperature (e.g., about 37° C.); in contrast, superelastic Ni—Ti used for medical devices is typically manufactured in the austenite phase at body temperature and superelastic Ni—Ti experiences an austenite to martensite phase transformation when stressed. The shapeable distal end section is shapeable by a user to facilitate guiding the guide wire through tortuous anatomy. In addition, linear pseudoelastic Ni—Ti alloy is more durable tip material than other shapeable tip materials, such as stainless steel. This may, for example, allow practitioners to use one wire to treat multiple lesions, potentially reducing costs and procedure time.

Guide wire devices are used in minimal invasive procedures such as, but not limited to, percutaneous transluminal coronary angioplasty (PTCA) to track through vessels, access and cross lesions, and support interventional devices for a variety of procedures. Because they are designed to track through a patient's vasculature, for example, guide wire devices may be quite long (e.g., about 150 cm to about 300 cm in length) and thin. Guide wire devices need to be long enough to travel from an access point outside a patient's body to a treatment site and narrow enough to pass freely through the patient's vasculature. For example, a typical guide wire device has an overall diameter of about 0.2 mm to about 0.5 mm for coronary use (e.g., about the diameter of the pencil leads typically used in automatic pencils). Larger diameter guide wires may be employed in peripheral arteries and other body lumens. The diameter of the guide wire device affects its flexibility, support, and torque. Thinner wires are more flexible and are able to access narrower vessels while larger diameter wires offer greater support and torque transmission.

II. Guide Wire Devices

In one embodiment of the present invention, a shapeable guide wire device is described. The shapeable guide wire device includes an elongate shaft member that includes a proximal end section and a shapeable distal end section having a solder material applied thereto. The shapeable distal end section includes a cold-worked linear nickel-titanium alloy exhibiting linear pseudoelastic deformation behavior imparted by cold work. The shapeable guide wire device further includes a helical coil section disposed about at least the shapeable distal end section, and an atraumatic cap section that is attached to (e.g., soldered to) the helical coil section and the shapeable distal end section. The atraumatic cap section may be formed from a bead of solder material that is applied to the helical coil section and the shapeable distal end section. According to the present embodiment, the atraumatic cap section is attached to the helical coil and the distal end section without loss of the linear elastic nickel-titanium microstructure.

Referring now to FIG. 1A, a partial cut-away view of a guide wire device 100 according to an embodiment of the invention is illustrated. The guide wire device 100 may be adapted to be inserted into a patient's body lumen, such as an artery. The guide wire device 100 includes an elongated proximal portion 102 and a distal portion 104. In one embodiment, the elongated proximal portion 102 may be formed from a first material such as stainless steel (e.g., 316L stainless steel) or a Ni—Ti alloy and the distal portion may be formed from a second material such as a Ni—Ti alloy. In another embodiment, the elongated proximal portion 102 and the distal portion 104 may be formed from a single material, such as a Ni—Ti alloy. If the elongated proximal portion 102 and the distal portion 104 are formed from different materials, the elongated proximal portion 102 and the distal portion 104 may coupled to one another via a welded joint 116 or another joint such as an adhesive joint, a brazed joint, or another suitable joint that couples the proximal portion 102 and the distal portion 104 into a torque transmitting relationship.

The distal portion 104 has at least one tapered section 106 that becomes smaller in diameter in the distal direction. The length and diameter of the tapered distal core section 106 can, for example, affect the trackability of the guide wire device 100. Typically, gradual or long tapers produce a guide wire device with less support but greater trackability, while abrupt or short tapers produce a guide wire device that provides greater support but also greater tendency to prolapse (i.e., kink) when steering.

The tapered distal core section 106 further includes a shapeable distal end section 108 that is formed from a Ni—Ti alloy in a linear pseudoelastic state. As will be discussed in greater detail below, the linear pseudoelastic state can be imparted upon Ni—Ti alloy by cold work. With increasing cold work, the elastic modulus of the linear section of the stress-strain curve increases, imparting different degrees of linear pseudoelasticity. Linear pseudoelastic Ni—Ti can readily be permanently deformed by stressing the material beyond its elastic strain limit. As such, the shapeable distal end section 108 can allow a practitioner to shape the distal and of the guide wire device 100 to a desired shape (e.g., a J-bend) for tracking through the patient's vasculature.

The Ni—Ti alloy portion(s) of the guide wire device 100 discussed herein, e.g., the distal portion 104, are, in some embodiment, made of an alloy material that includes about 30 to about 52% titanium and a balance nickel. The alloy may also include up to about 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. Cold worked Ni—Ti alloy portions (e.g., the shapeable distal end section 108) exhibit linear pseudoelastic behavior that is in the martensite phase without the appearance of stress-induced martensite upon deformation.

In one embodiment, the shapeable distal end section 108 is manufactured by, for example, drawing and grinding the distal end of the Ni—Ti distal section 104 to a first cross-sectional dimension, applying a solder material to the distal section 104, and cold-working (e.g., by flattening) the ground portion to a second cross-sectional dimension. In another embodiment, the shapeable distal end section 108 is manufactured by, for example, drawing and grinding the distal end of the Ni—Ti distal section 104 to a first cross-sectional dimension (e.g., a thickness or a diameter), cold-working a first time, applying a solder material to the distal section 104, and cold-working a second time (e.g., by flattening) the ground portion to a second cross-sectional dimension (e.g., a thickness). If cold working is performed prior to applying the solder material, it may be desirable to use a solder material with a sufficiently low melting temperature (e.g., as low as about 150° C.) such that a minimal amount of cold work is lost due to exposure to the molten solder.

The first dimension can be in a range from about 0.1 mm to about 0.07 mm, or about 0.08 mm. The second cross-sectional dimension, which is formed by, for example, cold-work flattening at least a part of the ground distal section, is in a range from about 0.065 mm to about 0.008 mm, about 0.055 mm to about 0.03 mm, about 0.05 to about 0.04 mm, or about 0.045 mm. In other words, the shapeable distal end section 108 is made from a Ni—Ti alloy that exhibits linear pseudoelastic deformation behavior imparted by about 20% to about 90% cold work, about 25% to about 65% cold work, about 40% cold work to about 50% cold work, or about 45% cold work.

The length of the shapeable distal end section 108 can, for example, affect the steerability of the guide-wire device 100. In one embodiment, the shapeable distal end section 108 is about 1 cm to about 10 cm in length, about 2 cm to about 6 cm in length, about 2 cm to about 4 cm in length, or about 2 cm in length.

As illustrated in FIG. 1A, the guide wire device 100 includes a helical coil section 110. The helical coil section 110 affects support, trackability, and visibility of the guide wire device and provides tactile feedback. In some embodiments, the most distal section of the helical coil section 110 is made of radiopaque metal, such as platinum or platinum-nickel alloys, to facilitate the observation thereof while it is disposed within a patient's body. The helical coil section 110 is disposed about all or only a portion of the distal portion 104 and the shapeable distal end section 108, and has a rounded, atraumatic cap section 120 on the distal end thereof. In some embodiments, the atraumatic cap section 120 is formed from a bead of solder applied to the helical coil section 110 and the shapeable distal end section 108. Typical solder materials that can be used for forming the atraumatic cap section 120 include 80/20 gold-tin or 95/5 silver-tin. However, other suitable types of medical-grade, lead-free solder can be used. The helical coil section 110 is secured to the distal portion 104 at proximal location 114 and at intermediate location 112 by a suitable solder material and/or a suitable adhesive.

Figure 1B:
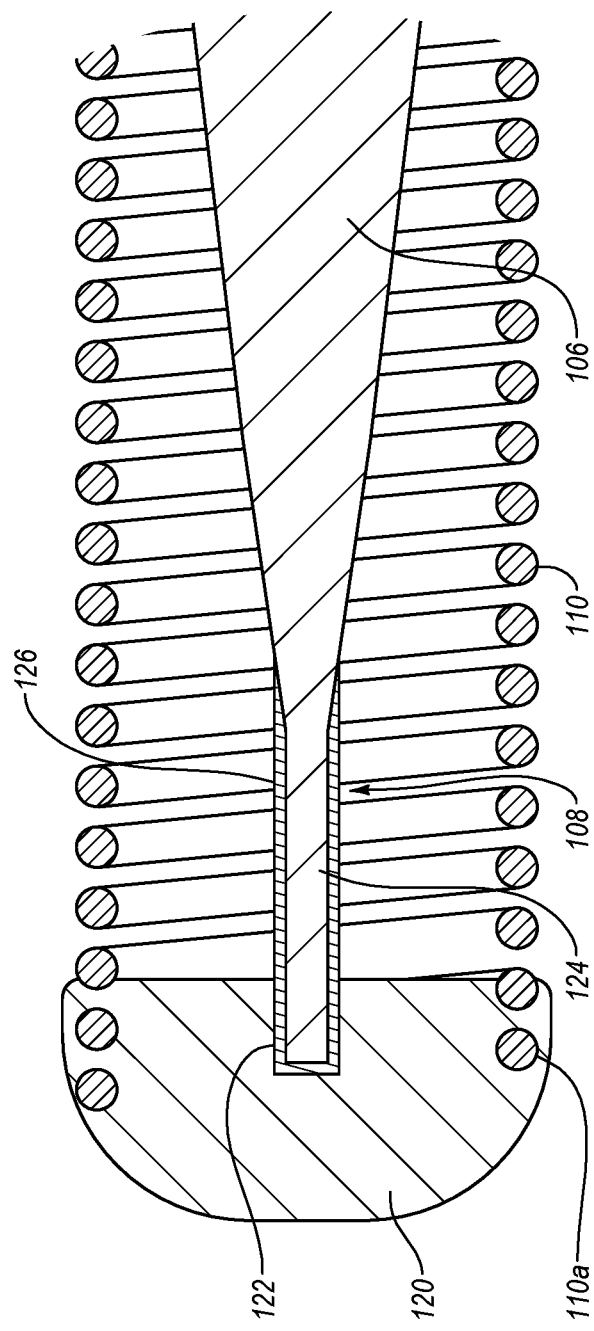
FIG. 1B illustrates an enlarged view of a distal end portion of the guide wire device illustrated in FIG. 1A.

Referring now to FIG. 1B, a cut-away view of an enlarged portion of the distal end of the guide wire device 100 is illustrated. The portion of the guide wire device 100 illustrated in FIG. 1B shows the tapered distal section 106, the shapeable distal end section 108, the helical coil section 110, and the atraumatic cap 120. The shapeable distal end section 108 includes a distal wire portion 124 composed of a Ni—Ti alloy that extends from the tapered distal section 106. As illustrated, the distal wire portion is coated with a layer of solder material 126 (e.g., a gold-tin solder, a gold-indium solder, a gold-germanium solder, a silver-tin solder, a silver-gold-tin solder, or another suitable solder). At least a portion of the distal wire portion 124 is cold worked after application of the layer of solder material 126 in order to form the shapeable distal end section 108.

The helical coil section 110 is attached to the shapeable distal end section 108 by soldering the rounded, atraumatic cap section 120 onto the helical coil section 110 and the shapeable distal end section 108. As illustrated, a portion 110a of the helical coil section 110 is embedded in the atraumatic cap 120, thus attaching the atraumatic cap 120 to the helical coil 120. The atraumatic cap 120 forms a soldered joint 122 with the shapeable distal end section 108 by forming a solder bond with the layer of solder material 126 that is in turn bonded to the distal wire portion 124. Because Ni—Ti alloy forms a persistent oxide layer, it can be difficult to solder Ni—Ti. Methods of manufacture will be discussed in detail below. However, because the distal wire portion 124 has a layer of solder material 126 bonded thereto, the atraumatic cap 120 can readily form a joint 122 with the shapeable distal end section 108. By using the methods and procedures described herein, the atraumatic cap 120 can be soldered to or formed on the shapeable distal end section 108 without significant loss of the linear pseudoelastic nickel-titanium deformation behavior.

In one embodiment, portions of the guide wire device 100 are coated with a coating 118 of lubricous material such as polytetrafluoroethylene (PTFE) (sold under the trademark Teflon by du Pont, de Nemours & Co.) or other suitable lubricous coatings such as the polysiloxane coatings, polyvinylpyrrolidone (PVP), and the like.

The guide wire device 100 that includes a Ni—Ti alloy portion 104 with a shapeable distal end section 108 having linear pseudoelastic characteristics, which facilitates shaping of the distal tip section 108 of the guide wire 100. The Ni—Ti alloy portion 104 may also include a superelastic portion proximal to the shapeable distal end section 108 to facilitate the advancing of the guide wire in a body lumen. The linear pseudoelastic and superelastic portions exhibit extensive, recoverable strain, which greatly minimizes the risk of damage to arteries during the advancement therein.

The proximal portion 102 of the guide wire device 100 is typically made from stainless steel. Stainless steel is generally significantly stronger, i.e., higher yield strength and ultimate tensile strength, than superelastic or linear pseudo elastic Ni—Ti. Suitable high strength materials include 304 or 316L stainless steel, which is a conventional material in guide wire construction.

Figure 2:
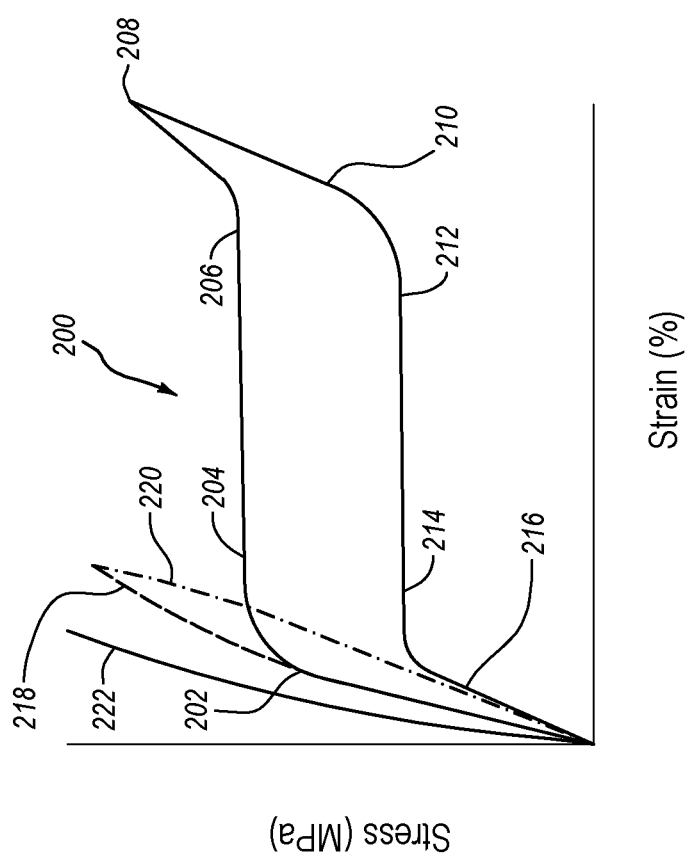
FIG. 2 illustrates stress-strain curves for stainless steel, a linear pseudoelastic Ni—Ti alloy, and a superelastic (i.e., non-linear pseudoelastic) Ni—Ti alloy.

To illustrate the foregoing points, FIG. 2 contains the elastic component of three idealized stress-strain curves for 316L stainless steel 222, linear pseudoelastic Ni—Ti 218/220, and non-linear pseudoelastic Ni—Ti alloy 200. The stress/strain relationship is plotted on x-y axes, with the x axis representing strain and the y axis representing stress.

In curve 200, when stress is applied to a specimen of a Ni—Ti alloy exhibiting non-linear pseudoelastic characteristics at a temperature at or above where the materials is in the austenitic phase, the specimen deforms elastically in region 202 until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve 200, this is represented by the upper, nearly flat stress plateau 204. The strain increases while the stress from continued deformation remains essentially constant until the transformation of the austenitic phase to the martensitic phase is complete at approximately region 206. Thereafter, further increase in stress is necessary to cause further deformation to point 208. The martensitic metal first yields elastically upon the application of additional stress and then plastically with permanent deformation (not shown).

If the load on the specimen is removed before any permanent deformation has occurred, the martensitic Ni—Ti alloy elastically recovers and transforms back to the austenitic phase. The reduction in stress first causes a decrease in strain along region 210. As stress reduction reaches the level at which the martensitic phase transforms essentially completely back into the austenitic phase at region 212, the stress level in the specimen remains essentially constant to continue relieving strain along lower plateau 214 (but less than the constant stress level at which the austenitic crystalline structure transforms to the martensitic crystalline structure until the transformation back to the austenitic phase is complete); i.e., there is significant recovery in strain with only negligible corresponding stress reduction.

After the transformation back to austenite is complete, further stress reduction results in elastic strain reduction along region 216. This ability to incur significant strain at relatively constant stress upon the application of a load and to recover from the deformation upon the removal of the load is commonly referred to as non-linear pseudoelasticity (or superelasticity).

FIG. 2 also includes a curve 218/220 representing the idealized behavior of linear pseudoelastic Ni—Ti alloy as utilized in the shapeable distal end section 108 in the present invention. The slope of curve 218/220 generally represents the Young's modulus of the linear pseudoelastic Ni—Ti alloy. Also, curve 218/220 does not contain any flat plateau stresses found in curve 200. This stands to reason since the Ni—Ti alloy of curve 218-220 remains in the martensitic phase throughout and does not undergo any phase change. To that end, curve 218/220 shows that increasing stress begets a proportional increase in reversible strain, and a release of stress begets a proportional decrease in strain. The areas bounded by curves 200 and 218-220 represent the hysteresis in the Ni—Ti alloy.

As is apparent from comparing curve 218/220 to curve 200 in FIG. 2, with the use of linear pseudoelastic Ni—Ti alloy, the mechanical strength of linear pseudoelastic Ni—Ti alloy and non-linear pseudoelastic Ni—Ti alloy is similar. Consequently, a major benefit of the distal end section 108 made from linear pseudoelastic Ni—Ti alloy is that it is shapeable, whereas a distal end section made from non-linear pseudoelastic Ni—Ti alloy is practically un-shapeable because it is very difficult to overstrain non-linear pseudoelastic Ni—Ti alloy.

FIG. 2 also includes curve 220 which is the elastic behavior of a standard 316L stainless steel. Stress is incrementally applied to the steel and, just prior to the metal deforming plastically, decrementally released.

III. Methods for Fabricating a Guide Wire Device

In one embodiment, a method for fabricating a guide wire device is disclosed. The method includes (1) fabricating an elongate shaft member that includes a proximal end section and a distal end section. In one embodiment, the distal end section includes a nickel-titanium alloy member that has a first cross-sectional dimension (e.g., a thickness). The method further includes (2) dipping at least a portion of the distal end section in a molten solder material to apply (e.g., coat) the molten solder material thereon, (3) cold working at least a portion of the distal end section having the solder material coated thereon, wherein the cold working yields a distal shapeable section having a linear pseudoelastic nickel-titanium microstructure, and (4) soldering the distal shapeable section and a helical coil section disposed about the distal shapeable section to an atraumatic cap without substantial loss of the linear pseudoelasticity of the distal shapeable section.

In one embodiment, fabricating an elongate shaft member that includes a proximal end section and a distal end section may include may include attaching (e.g., by welding) a proximal end section fabricated from a first material such as stainless steel to a distal end section fabricated from a second material such as nickel-titanium alloy. Alternatively, the elongate shaft member can be fabricated from a single material such as, but not limited to, a nickel-titanium alloy.

In one embodiment, fabricating an elongate shaft member may further include drawing at least a portion of the elongate shaft member through a drawing die, rolling, calendaring, grinding, or combinations thereof to form or reshape the at least a portion of the elongate shaft member and cleaning the elongate shaft member such as by ultrasonically cleaning.

Ni—Ti alloys, such as those described herein, are very difficult to solder due to the formation of a tenacious, naturally occurring oxide coating which prevents the molten solder from wetting the surface of the alloy. It has been found that by first treating the surface of the Ni—Ti alloy with molten alkali metal hydroxide, e.g., sodium, potassium, lithium or mixtures thereof to form a substantially oxide-free alloy surface and then pretinning (i.e., applying a suitable solder material, such as, a gold-tin solder, a gold-indium solder, a gold-germanium solder, a silver-tin solder, a silver-gold-tin solder, or another suitable solder) without contacting air, that Ni—Ti alloys can be readily soldered in a conventional manner. In one embodiment, solder can be applied to at least a portion of the distal end section by dipping the at least the distal end section into a bath, wherein the bath includes an upper layer of a molten metal hydroxide and a lower layer of the molten solder material. Alternatively, a layer of solder material can be applied to at least a portion of the distal end section by chemical vapor deposition (CVD), physical vapor deposition (PVD), sputter coating, and the like, and combinations thereof.

Subsequently, at least a portion of the distal end section, with the solder material applied thereto, can be cold-worked to yield a distal shapeable end section having a second cross-sectional dimension. After applying the solder material and cold working, a helical coil section can be assembled around the a distal portion of the elongate shaft member, including the distal shapeable section, and a rounded plug (i.e., an aturaumatic cap section) can be formed at the distal end of the assembly by soldering the distal shapeable section and a helical coil section disposed about the distal shapeable section to the rounded plug without substantial loss of the linear pseudoelasticity of the distal shapeable section. The pretinning followed by cold working and forming the atraumatic cap at the distal end of the elongate shaft member yields a user-shapeable distal end section that exhibits linear pseudoelastic deformation behavior without a phase transformation or onset of stress-induced martensite.

In a more specific embodiment, a method for fabricating a guide wire device that has a shapeable distal end section includes (1) providing an elongate shaft member that includes a proximal end section and a distal end section, wherein the distal end section includes a nickel-titanium alloy member, (2) grinding at least a portion of the distal end section to a first cross-sectional dimension, and (3) ultrasonically cleaning at least the distal end section. After grinding and cleaning, the method further includes (4) dipping at least a portion of the distal end section into a bath of a molten solder material, wherein the bath of molten solder material includes an upper layer of a molten metal hydroxide and a lower layer of the molten solder material, and (5) cold working at least a portion of the distal end section, wherein the cold working yields a distal shapeable section having a linear pseudoelastic nickel-titanium microstructure. After cold working at least a portion of the distal end section, the method continues with (6) ultrasonically cleaning at least the distal end section, (7) disposing a helical coil section about the distal shapeable section, and (8) forming an atraumatic cap section coupling the helical coil section and the distal shapeable section via a soldered joint, wherein the soldered joint is formed without loss of the linear elastic nickel-titanium microstructure.

Ni—Ti alloys, such as those described herein, are very difficult to solder due to the formation of a tenacious, naturally occurring oxide coating which prevents the molten solder from wetting the surface of the alloy in a manner necessary to develop a sound, essentially oxide free, soldered joint. It has been found that by first treating the surface of the Ni—Ti alloy with molten alkali metal hydroxide, e.g., a hydroxide of sodium, potassium, lithium, or mixtures thereof to form a sufficiently oxide free alloy surface and then pretinning with a suitable solder such as a gold-tin solder or the like without contacting air, that the Ni—Ti piece can be readily soldered in a conventional manner.

A presently preferred alkali metal hydroxide is a mixture of about 59% KOH and about 41% NaOH. The solder may have a melting point temperature in a range of about 150° C. to about 350° C. or about 280° C. to about 300° C. The solder may contain from about 60 to about 85% gold and the balance tin, with the presently preferred solder containing about 80% gold and about 20% tin. Other suitable solders may include gold-indium, gold-germanium, silver-tin, and silver-gold-tin.

In a presently preferred procedure, a multilayered bath is provided with an upper layer of molten alkali metal hydroxide and a lower layer of molten gold-tin solder. The part of the superelastic distal portion, which is to be soldered, is thrust into the multilayered bath through the upper surface of the molten alkali metal hydroxide which removes the oxide coating, leaving a sufficiently oxide free alloy surface, and then into the molten solder which wets the cleaned surface. When the solder solidifies upon removal from the molten solder into a thin coating on the metal alloy surface, the underlying alloy surface is protected from the oxygen-containing atmosphere. Any of the alkali metal hydroxide on the surface of the solder can be easily removed with water without detrimentally affecting either the pretinned layer or the underlying alloy surface. The pretinned Ni—Ti member is then ready for further processing and/or soldering. The pretinning procedure may be employed for soldering other metal alloys having significant titanium levels.

In one embodiment, the distal end section may be drawn and ground to a first dimension (e.g., about 0.08 mm), ultrasonically cleaned, and pretinned according to the method described above. In one embodiment, the distal end section can be dipped in the molten solder material at least a second time if a thicker coating of solder is desired or if the distal end section was not completely coated in the first dip. After pretinning, the distal end section is cold-worked, ultrasonically cleaned, and soldered using conventional soldering procedures.

Suitable examples of cold working procedures that can be used to cold work the distal end section include, but are not limited to, high force flattening, stamping, rolling, calendaring, and combinations thereof. High force flattening is the currently preferred cold-working procedure.

Figure 3:
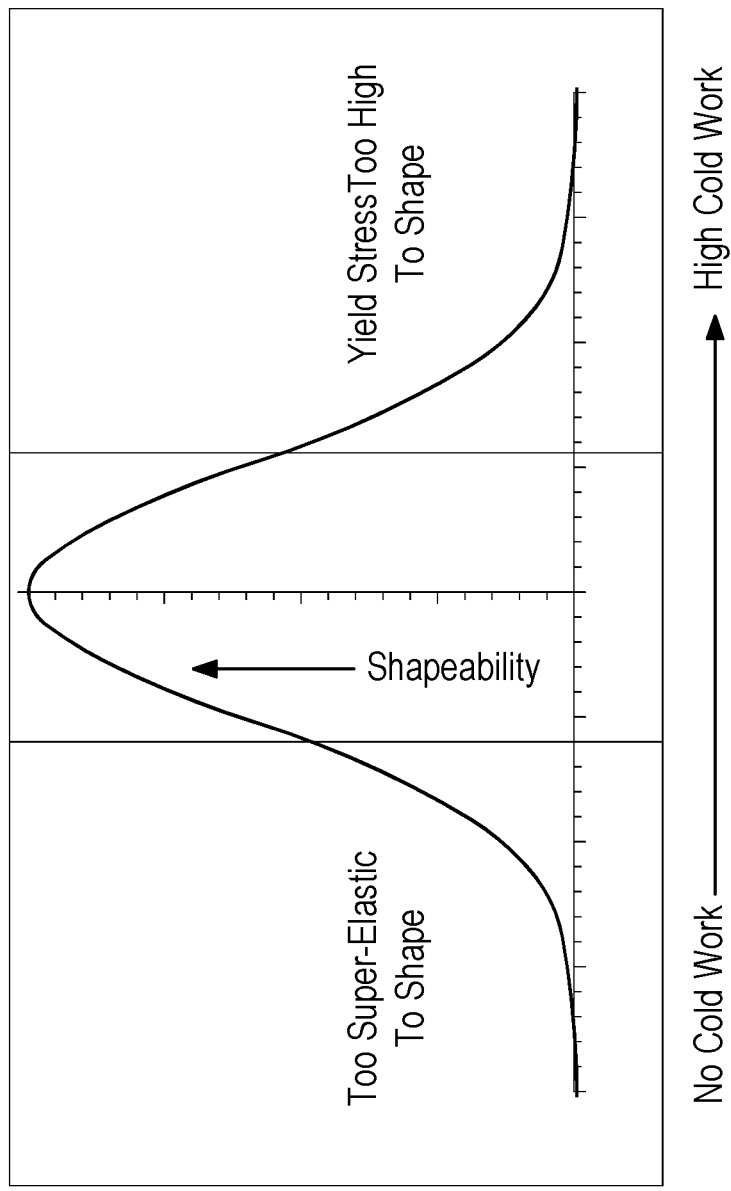
FIG. 3 is a diagram schematically illustrating the relationship between degree of cold work and shapeability of a Ni—Ti alloy.

The cold working procedure and the degree of cold working is important for obtaining a distal end section that is shapeable by a user. This is graphically illustrated in FIG. 3. FIG. 3 is a diagram schematically illustrating the relationship between degree of cold work and shapeability of a Ni—Ti alloy. As can be seen in FIG. 3, when superelastic Ni—Ti has little or no cold work, the material has too much superelastic character to be shaped. At the other end of the spectrum, Ni—Ti alloy material that has too much cold work becomes essentially unshapeable by manual means because its yield stress is too high. That is, highly cold-worked Ni—Ti alloy may be shapeable, but the stress that must be exceeded to exceed the elastic limit of the material (i.e., the yield stress) is too high to be conveniently shaped by hand. In the middle of the spectrum, there is shown a region where the degree of cold work is such that the Ni—Ti material is highly shapeable.

Figure 4:
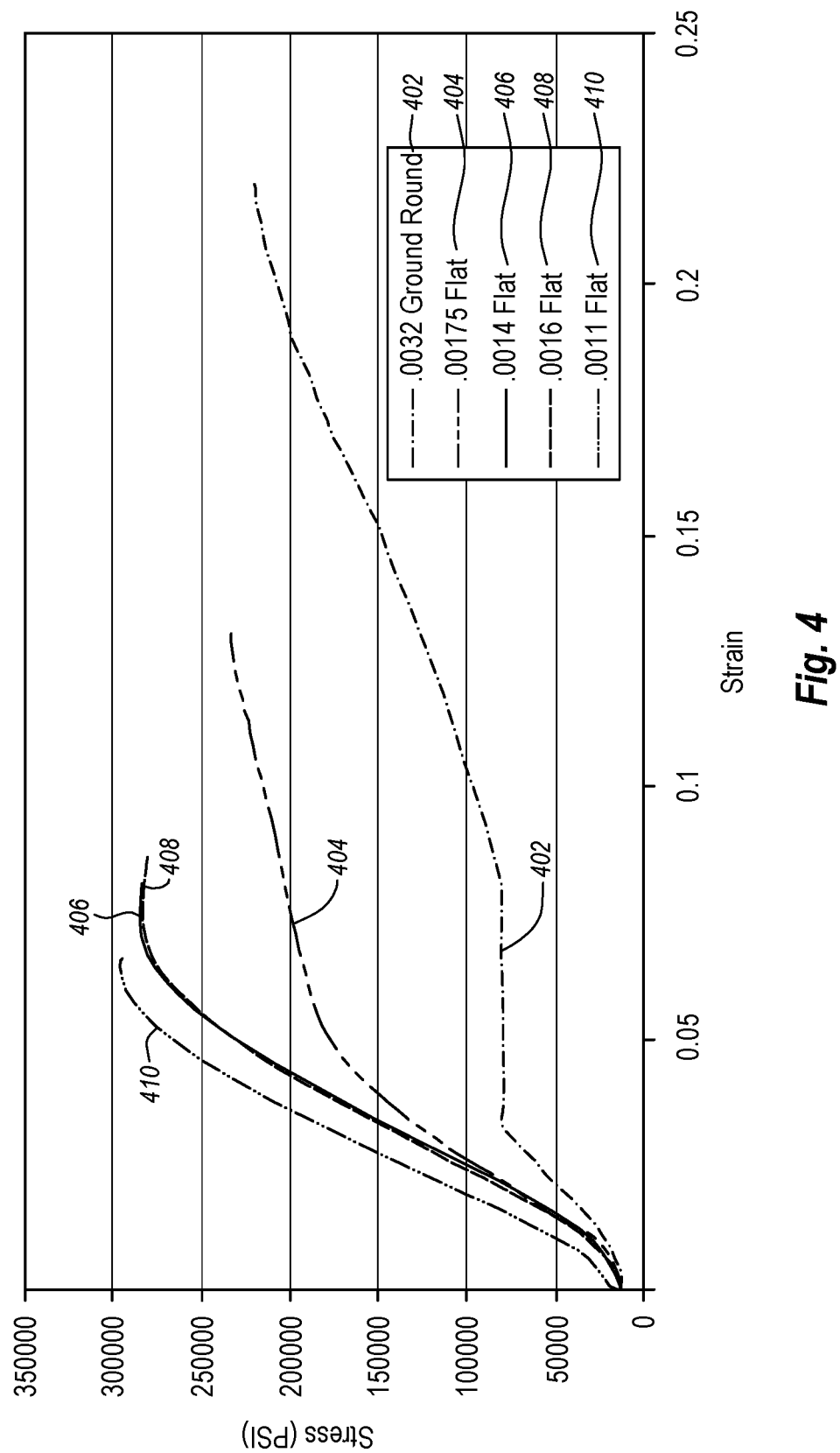
FIG. 4 is a diagram illustrating the yield stress of samples of Ni—Ti alloy having various degrees of cold work.

Specific examples of this phenomenon are illustrated in FIG. 4, which illustrates the yield stress of samples of Ni—Ti alloy having various degrees of cold work. The as-ground (0.08 mm) sample is illustrated at curve 402. The superelastic, as-ground material cannot be permanently deformed with any degree of reliability. Curves 404-410 illustrate the effect associated with increasing amounts of cold work. The sample illustrated in curve 404 was flattened from the as-ground diameter of about 0.08 mm to about 0.045 mm, which corresponds to about 45% cold work. The sample illustrated in curve 404 has a yield stress of about 1200 MPa (~175 ksi). The samples illustrated in curves 406 and 408 were flattened from the as-ground diameter of about 0.08 mm to about 0.041 mm and 0.036 mm (respectively), which corresponds to about 49-55% cold work. The samples illustrated in curves 406 and 408 have yield stresses of about 1900 MPa (~275 ksi). The sample illustrated in curve 410 was flattened from the as-ground diameter of about 0.08 mm to about 0.028 mm, which corresponds to about 65% cold work. The sample illustrated in curve 410 has a yield stress of about 2070 MPa (~300 ksi).

Based on the results illustrated in FIG. 4, the distal shapeable section can be cold-worked to have a yield stress in a range of about 690 MPa (~100 ksi) to about 2070 MPa (~300 ksi) or about 1034 MPa (~150 ksi) to about 1380 MPa (~200 ksi). Yield stresses in these ranges are obtained when the distal shapeable section that has a cold-worked microstructure that includes about 25% to about 65% cold work, about 40% to about 50% cold work, or about 45% cold work.

Figure 5:
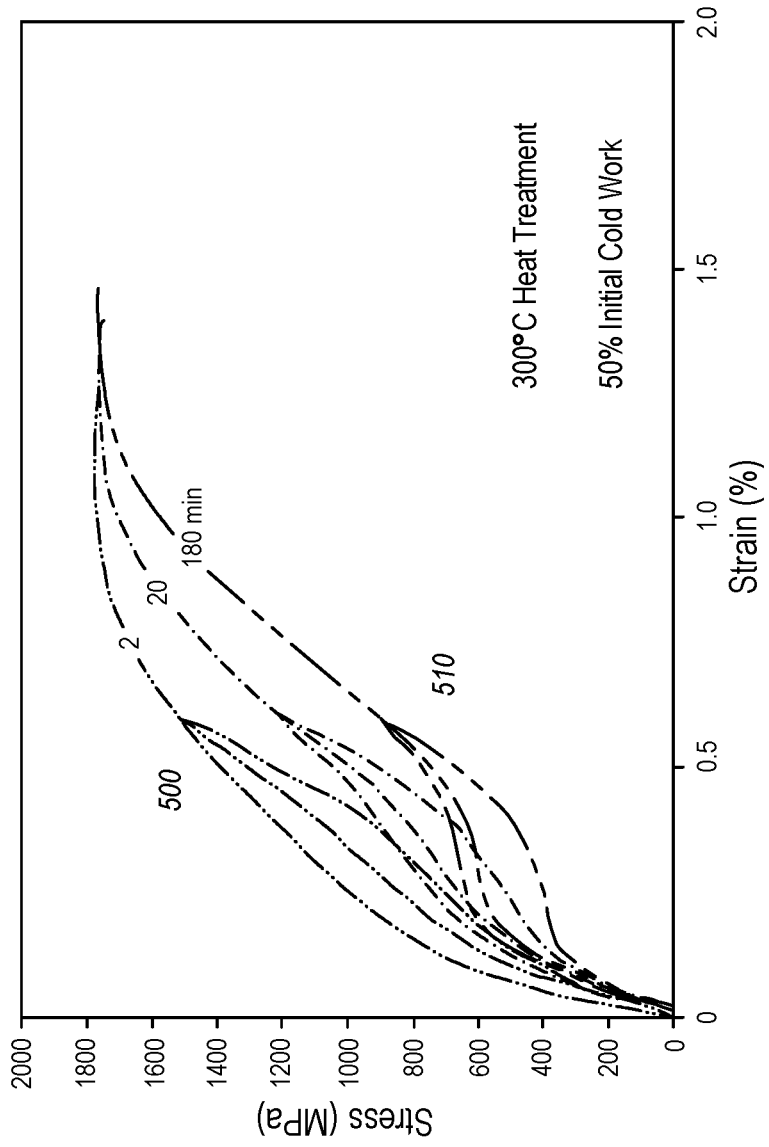
FIG. 5 is a diagram illustrating loss of linear pseudoelastic character of Ni—Ti alloy as a result of moderate heat exposure for varying amounts of time.

The linear pseudoelastic microstructure can be lost if the Ni—Ti material is heated after cold working. This is illustrated in FIG. 5, which shows the progressive loss of linear pseudoelastic character of Ni—Ti alloy as a result of moderate heat exposure for varying amounts of time. FIG. 5 illustrates the loss of cold work in three samples of cold-worked Ni—Ti alloy having been exposed to 300° C. heat treatment for 2 minutes, 20 minutes, and 180 minutes. Curves in region 500 show more linear pseudoelastic behavior, while curves in region 510 show more superelastic behavior. All curves show potentially significant loss of cold work induced linear pseudoelastic behavior.

Comparing the results of FIGS. 4 and 5, it is apparent why it is important to pretin and then cold work as opposed to cold working followed by pretinning. That is, it can be seen that the yield stress is relatively sensitive to the amount of cold work. For example, samples 406 and 408 have relatively similar amount of cold work, yet their yield stresses are considerably different. In order to obtain a distal shapeable section that can be reliable shaped, it is important to carefully select the amount of cold work. On the flip side, it is important to not lose that cold work by pretinning after cold working.

While it is believed that pretinning after cold working may lead to loss of cold work, it is not believed that soldering leads to significant loss of cold work in the distal shapeable section. This is believed to be due to the fact that soldering involves only localized application heat as opposed to solder dipping, which involves general application of heat that could lead to potentially significant loss of cold work induced linear pseudoelastic behavior.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A shapeable medical device configured to allow a practitioner to shape a distal end to a desired shape for tracking through a patient's vasculature, the shapeable medical device comprising:
   an elongate shaft member comprising:
      an elongate proximal portion;
      a distal portion extending distally from the elongate proximal portion, the distal portion comprising a distal end portion comprising a proximal end section and a practitioner-shapeable distal end section, wherein the proximal end section is formed of a material that does not exhibit superelasticity and the practitioner-shapeable distal end section (i) being formed of a nickel titanium alloy, (ii) in a martensite phase at body temperature and having a stress-strain curve without any flat plateau stresses, (iii) with a metallic material applied over and coating an entirety of the nickel titanium alloy and a portion of the proximal end section of the distal end portion, a proximal terminal end of the metallic material being distal a proximal terminal end of the proximal end section, (iv) such that the practitioner-shapeable distal end section does not exhibit a phase transformation or onset of stress-induced martensite as the practitioner-shapeable distal end section is stressed and is linear pseudoelastic;

a second distal portion between the proximal end section and the practitioner-shapeable distal end section, wherein the second distal portion between the proximal end section and the distal end section comprises a superelastic nickel-titanium alloy, and wherein (i) the proximal end section comprises a material that does not exhibit superelasticity and (ii) the distal end section is linear pseudoelastic;

a helical coil section disposed around at least the practitioner-shapeable distal end section; and an atraumatic cap section attached to the helical coil section and the metallic material of the practitioner-shapeable distal end section, wherein a portion of the helical coil is embedded in the atraumatic cap section and the practitioner-shapeable distal end section has a yield stress from 100 ksi to 300 ksi and exhibits 20% to 90% cold work.

2. The shapeable medical device of claim 1, wherein the elongate shaft member comprises stainless steel, a superelastic nickel-titanium alloy, or a combination thereof.

3. The shapeable medical device of claim 1, wherein the practitioner-shapeable distal end section has a yield stress in a range of 150 ksi to 225 ksi.

4. The shapeable medical device of claim 1, wherein the practitioner-shapeable distal end section has a yield stress in a range of 150 ksi to 200 ksi.

5. The shapeable guide wire device of claim 1, wherein a core of the distal end section surrounded by the metallic material consists of the nickel titanium alloy.

6. The shapeable medical device of claim 1, wherein the practitioner-shapeable distal end section has a yield stress in a range of 150 ksi to 200 ksi and the nickel-titanium alloy exhibits 40% to 50% cold work.

7. The shapeable medical device of claim 1, wherein the atraumatic cap section comprises a cap of solder and wherein the solder material includes a eutectic alloy.

8. The shapeable medical device of claim 7, wherein the eutectic alloy comprises a gold-tin solder, a gold-indium solder, a gold-germanium solder, a silver-tin solder, or a silver-gold-tin solder.

9. The shapeable medical device of claim 7, wherein the gold-tin solder includes 80 weight % (wt %) gold and 20 wt % tin.

10. The shapeable medical device of claim 1, wherein the atraumatic cap section comprises a cap of solder soldered to the helical coil section and the practitioner-shapeable distal end section.

11. The shapeable medical device of claim 1, wherein the metallic material has a melting temperature of about 150° C.

12. The shapeable medical device of claim 1, wherein a distal section of the helical coil section is made of radiopaque material.

13. The shapeable medical device of claim 1, wherein the helical coil section is secured to the distal portion at a proximal location and at an intermediate location.

14. The shapeable medical device of claim 1, wherein one or more portions of the shapeable medical device are coated with a lubricous material.

* * * * *